United States Patent [19]

Takahashi

[11] Patent Number: 4,978,536

[45] Date of Patent: Dec. 18, 1990

[54] NOVEL SYNTHETIC ALUMINUM SILICATE PREPARATION

[75] Inventor: Hidehiko Takahashi, Tokyo, Japan

[73] Assignee: Yakurigaku Chuo Kenkyusho, Tokyo, Japan

[21] Appl. No.: 195,045

[22] Filed: May 17, 1988

[30] Foreign Application Priority Data

May 19, 1987 [JP] Japan ................. 62-121674

[51] Int. Cl.$^5$ .............................. A61K 33/06
[52] U.S. Cl. ................... 424/684; 514/926; 514/927
[58] Field of Search ................. 424/154, 684

[56] References Cited

U.S. PATENT DOCUMENTS 4,536,394  8/1985  Bernat ................. 424/154
4,537,771  8/1985  Greb et al. ............ 424/684

FOREIGN PATENT DOCUMENTS 58-54087  12/1983  Japan .

OTHER PUBLICATIONS

Patent Abstracts of Japan, vol. 5, No. 8 (C-39) (680), Jan. 20, 1981; & JP-A-55 136118 (Yakurigaku) 23.10.1980.
Patent Abstracts of Japan, vol. 7, No. 56 (C-155) (1201), Mar. 8, 1983; & JP-A-57 207543 (Yakurigaki) 20.12.1982.

*Primary Examiner*—Frederick E. Waddell
*Attorney, Agent, or Firm*—Armstrong, Nikaido, Marmelstein, Kubovcik & Murray

[57] ABSTRACT

Disclosed is use of a synthetic aluminum silicate as antacid and anti-ulcer preparation, anti-obesity preparation and acne curing preparation. This aluminum silicate is obtained by reacting an aluminum compound and silicic acid or water glass at a weight ratio $Al_2O_3$: $SiO_2$ of 4.5:1.0-6.0:1.0 in a strongly acidic aqueous solution having an initial pH of 1.0-3.0, then adding thereto a basic substance to reach excess in alkali and then neutralizing the reaction mixture to pH 5.0-7.0 with an acid.

1 Claim, 2 Drawing Sheets

NOVEL SYNTHETIC ALUMINUM SILICATE PREPARATION

BACKGROUND OF THE INVENTION

The present invention relates to a novel synthetic aluminum silicate composition and, more particularly, it relates to an antacid and anti-ulcer preparation mainly composed of "Takallophane" which is an aluminum silicate.

Natural or synthetic aluminum silicate or its composition has been known to have particular selective adsorptive and catalytic actions and have been used in various fields. However, biological or clinical applications thereof have not been known before starting of study by the inventor except for preparation for curing intestinal disorder of natural aluminum silicate and antacid preparation of synthetic aluminum silicate. However, the antacid action thereof is weak and researches for increasing the antacid action have been made by various chemical modifications of the aluminum silicates. Such methods to increase the antacid action have suffered from problems such as increase of production cost, increase of toxicity and sometimes bitter or unpleasant taste. Besides, research and development up to now have not been made on adsorptive action of aluminum silicate.

Under the circumstances, the inventor has already succeeded in production of aluminum silicate high in antacid action and having selective adsorptive action and obtained Japanese Pat. No. 1,223,379 on this method and application of the product to adsorption of melanin. During studying of this method, it has been found that a great change occurs in selectivity in adsorptive action by a slight modification of the method and ratio of $SiO_2/Al_2O_3$.

Based on this finding, the inventor has completed a method for preparation of aluminum silicate strong in adsorption of free fatty acids and bile acid salts and high in antacid power and has succeeded in development of uses of the resulting synthetic aluminum silicate having both the antacid action and adsorption action as various medicines and cosmetics.

None of the conventionally known natural and synthetic aluminum silicates are satisfactory in one or both of antacid and adsorptive actions and so use thereof has been limited as mentioned above and exploitation of new useful uses has been hoped for by preparation of synthetic aluminum silicate superior in both the antacid action and adsorptive action.

SUMMARY OF THE INVENTION

According to the present invention, there are provided new uses of the aluminum silicate (referred to as "Takallophane" hereinafter) obtained by the method disclosed in the inventor's Japanese Pat. No. 1,223,379 and having both the antacid action and adsorptive action, namely, synthetic aluminum silicate obtained by reacting an aluminum compound with silicic acid or water glass at a weight ratio of $Al_2O_3:SiO_2$ of 4.5:1.0–6.0:1.0 in a strongly acidic aqueous solution of initial pH 1.0–3.0, then adding thereto a basic substance until alkali becomes excess and then neutralizing the reaction mixture to pH 5.0–7.0 with acid. The new uses provided include antacid and anti-ulcer preparations, anti-obesity preparations having also the effects of reduction of neutral fat and cholesterol and acne treating preparations which contain said synthetic aluminum silicate as an active ingredient.

DESCRIPTION OF THE INVENTION

The synthetic aluminum silicate obtained as mentioned above is characterized by much higher aluminum content than the conventional aluminum silicates. That is, the conventional aluminum silicates have the compositions $Al_2O_3.SiO_3.5H_2O$, $3Al_2O_3.2SiO_2$, $Al_2O_3.2SiO_2.2H_2O$, etc. while the synthetic aluminum silicate used in the present invention is a hydrated aluminum silicate represented by $xAl_2O_3.SiO_2.yH_2O$ (wherein $x=2-5$ and $y=18-20$). Properties of this substance will be explained below by way of example.

EXAMPLE 1 Antacid effect of Takallophane

Figure 1:
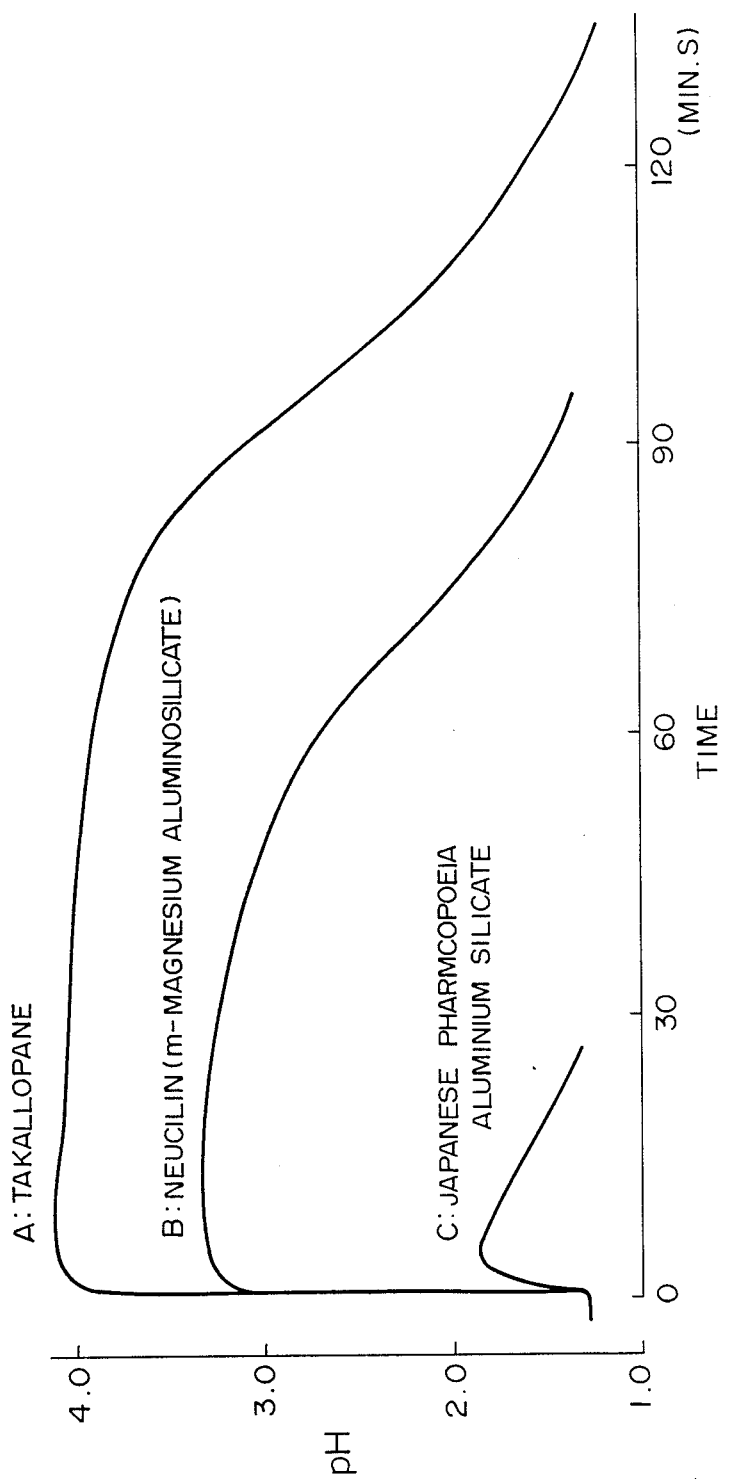
FIG. 1 is a graph which shows antacid action of the synthetic aluminum silicate preparation of the present invention in comparison with those of conventional preparations by pH curve according to the modified Fuchs' method. In the graph, curve A is time-pH curve of Takallophane of the present invention, curve B is that of Neusilin (meta-magnesium aluminosilicate supplied by Fuji Chemical Industry Co.) and curve C is that of Japanese pharmacopoeial aluminum silicate.

Antacid power according to the Japanese Pharmacopoeia was 240 ml or higher. FIG. 1 shows pH curves according to the modified Fuchs' method. It can be seen therefrom that the antacid effect of the preparation of the present invention is remarkably higher than that of pharmacopoeial grade aluminum silicate (50 ml or higher) and is even superior to that of Neusilin which is a new antacid and has strong action.

EXAMPLE 2 Anti-ulcer effect on Shay rat

Neusilin and Takallophane were compared for their anti-ulcer effect on acutely inflamed Shay rat (male Wistar). The effect was nearly the same. The results are shown in the following Table.

| | | Effect on ulcer and secretion of gastric juice | | | | | | |
|---|---|---|---|---|---|---|---|---|
| | | | | | | | Secretion of gastric juice $m \pm SE$ | |
| | | Number of rat | b.w $m \pm SE$ | Ulcer index $m \pm SE$ | Inhibitory rate % | Number of rats | vol. ml | pH |
| Control | | 20 | 185.6 ± 1.4 | 4.4 ± 0.3 | | 19 | 9.9 ± 0.5 | 2.47 ± 0.15 |
| Talkallophane | 222 mg/kg | 10 | 189.2 ± 2.9 | 1.6* ± 0.5 | 63.6 | 10 | 9.7 ± 0.9 | 3.59* ± 0.26 |
| | 333 | 10 | 180.0 ± 1.6 | 0.9* ± 0.3 | 79.5 | 10 | 12.8* ± 0.9 | 3.88* ± 0.14 |
| | 500 | 10 | 186.1 ± | 0.5* ± | 88.6 | 10 | 12.5* ± | 4.51* ± |

-continued

Effect on ulcer and secretion of gastric juice

|  | Number of rat | b.w m ± SE | Ulcer index m ± SE | Inhibitory rate % | Number of rats | Secretion of gastric juice m ± SE | |
|---|---|---|---|---|---|---|---|
|  |  |  |  |  |  | vol. ml | pH |
| Neusilin | 222 | 10 | 190.8 ± 3.3 | 1.2 ± 2.2* ± 0.6 | 50.0 | 8 | 10.0 ± 1.1 | 0.8 ± 3.52* ± 0.29 |
|  | 333 | 10 | 182.9 ± 1.5 | 1.2* ± 0.3 | 72.7 | 10 | 13.8* ± 0.6 | 3.74* ± 0.10 |
|  | 500 | 10 | 185.0 ± 2.4 | 0.5* ± 0.2 | 88.6 | 10 | 14.9* ± 0.7 | 4.26* ± 0.18 |

*$P < 0.01$

EXAMPLE 3 Anti-acne action of Takallophane

Adsorption power of Takallophane for free factty acids is shown in the following table. This test was effected under the following conditions: Takallophane: 2.5%; shaking: 60 minutes; concentration of fatty acid: 0.5%; and determination of amount of fatty acid: improved Itaya-Ui method (Kuki et al, 1970).

| | Adsorptivity (%) | | | | | |
|---|---|---|---|---|---|---|
| Fatty acid | Lauric acid | Palmitic acid | Palmitoleic acid | Oleic acid | Linoleic acid | Linolenic acid |
| | 81 | 46.3 | 96.4 | 72.0 | 69.0 | 26.0 |

Turnover of human keratin layer according to fluorescence staining technique using 5% dansyl chloride reduced to about 9 days under application of 5% Takallophane from 14 days of blank.

Effect of 5% Takallophane lotion on actual acne patients was determined by observing the acne part after application of the lotion to 10 males and females of 18–23 years old twice a day for one month. The patients were all ordinary acne patients. The effect was remarkable (completely cured) in all cases.

EXAMPLE 4 Adsorbing test for sodium glycocholate 0.1% Sodium glycocholate was stirred at room temperature for 1 hour and then supernatant liquid was mixed with sulfuric acid reagent and absorbance for 318 nm was measured. The results are as follows.

| Adsorbent | Concentration (%) | Adsorptivity (%) |
|---|---|---|
| Takallophane | 0.2 | 15 |
|  | 1.0 | 51 |

Comparison of adsorptivity for sodium glycocholate (1.0%) was made. The results are shown below.

| Adsorbent | Concentration (%) | Adsorptivity (%) |
|---|---|---|
| Takallophane | 1.0 | 20 |
| Chitin | 1.0 | 16 |
| Chitosan | 1.0 | 8 |

Human bile acid salt comprises glycin conjugate and taurine conjugate and it has been known that the glycin conjugate is 75 mol% of the salt. The representative one, glycocholate was used here.

EXAMPLE 5 Preparation of formulation of Takallophane with enteric coating

Formulation of enteric coating solution

| Compound | W/W % |
|---|---|
| Hydroxypropylmethyl cellulose phthalate (HP 55) | 10 |
| Acetone | 67 |
| Isopropyl alcohol | 23 |

For preparation of the above formulation, HP 55 was gradually added to acetone and isopropyl alcohol with well stirring to dissolve HP 55. This took several hours. To this coating solution was added Takallophane so that concentration of HP 55 in the formulation reached 5.5% and then the organic solvent was devolatilized to obtain fine granules.

EXAMPLE 6 Effect I obtained by administration of the enteric coating granules of Takallophane Fifteen Wistar SPF male rats were divided into 3 groups with 5 rats for each group. Only feeds [powder chow (Clea C-2)] were given to the rats of the first group, feeds containing 10% hydroxypropylmethyl cellulose phthalate were given to the rats of the second group and feeds containing 10% of the above enteric coating Takallophane were given to the rats of the third group.

Intake of feeds was nearly the same for the rats of all groups, but weight gain of the rats of the third group was conspicuously low. (cf. FIG. 2). Hematochemically, conspicuous reduction of triglyceride content was recognized in the third group.

Figure 2:
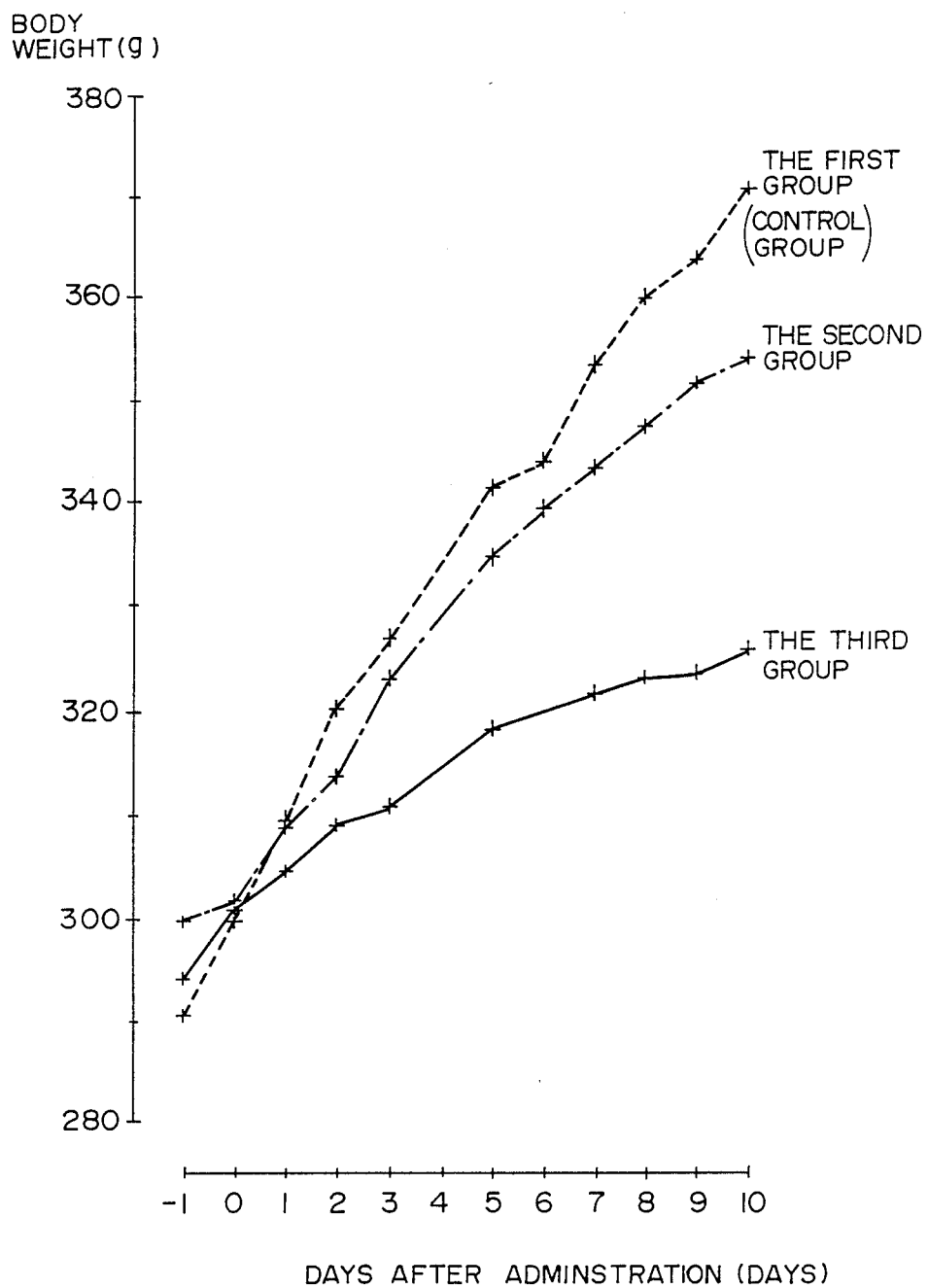
FIG. 2 is a graph which shows anti-obesity action of the preparation of the present invention according to animal (rats) tests.

The results are shown in the following table and FIG. 2.

|  | The first group (Control) | The second group (Feed containing coating material) | The third group (Test group) |
|---|---|---|---|
| Initial body weight (g) | 300.0 ± 10.2 | 302.8 ± 2.8 | 301.0 ± 8.6 |
| Final body weight (g) | 370.8 ± 15.9 | 354.3 ± 6.5 | 325.8 ± 11.7 |
| Total cholesterol (mg/dl) | 82.8 ± 5.2 | 74.5 ± 2.1 | 76.5 ± 3.3 |
| Triglyceride (Neutral fats) (mg/dl) | 139.0 ± 16.4 | 101.8 ± 23.3 | 46.3 ± 10.3 |

*Stochastically significant reduction ($P < 0.05$)

EXAMPLE 7 Effect II by administration of the enteric coating granules of Takallophane Wistar SPF female rats were bred with feeds of high fats and high carbohydrates for 47 days. After weight gain increased significantly ($p<0.05$) as compared with the rats bred with standard feeds (control), the rats were divided into two groups and those of one group were bred with feeds of high fats and high carbohydrates (control group) and those of another group were bred with feeds of high fats and high carbohydrates and containing 10% Takallophane enteric preparation (test group) for 14 days. The results are shown below.

|  | Final body weight (average value + standard deviation value) (g) |
| --- | --- |
| Standard feed group | 329.0 ± 7.8 |
| Control group | 378.7 ± 11.5 |
| Test group | 353.4 ± 13.3 |

No significant difference ($p>0.05$) was recognized between average body weight of control group and that of test group, but it cannot be denied that 10% Takallophane has inhibitive action on increase of body weight ($0.1>p>0.05$).

According to hematochemical measurement, the following results should be noticed. That is, concentrations of triglyceride and total cholesterol in blood were significantly ($p<0.05$) decreased by administration of Takallophane.

|  | Control group | Test group |
| --- | --- | --- |
| Triglyceride (mg/dl) | 96.0 ± 13.0 | 67.0 ± 13.5 |
| Total cholesterol (mg/dl) | 63.0 ± 5.5 | 42.4 ± 9.8 |

What is claimed is:

1. A method of lowering the acidity of gastric juice or treating a gastric ulcer, which comprises administering to an animal in need of such therapy, an antacid effective amount of an aluminum silicate of the formula $xAl_2O_3 \cdot SiO_2 \cdot yH_2O$, wherein $x=2-5$ and $y=18-20$, obtained by reacting an aluminum compound and at least one compound selected from the group of silicic acid and water glass at a weight ratio $Al_2O_3:SiO_2$ of 4.5:1.0–6.0:1.0 in a strongly acidic aqueous solution having an initial pH of 1.0–3.0, adding a basic substance to provide an excess amount of alkali, and neutralizing to pH 5.0–7.0 with an acid.

* * * * *